(12) United States Patent
Rigal et al.

(10) Patent No.: US 8,785,608 B2
(45) Date of Patent: Jul. 22, 2014

(54) CRYSTALLINE HETEROAROMATIC FLUOROGLYCOSIDE HYDRATES, PHARMACEUTICALS COMPRISING THESE COMPOUNDS AND THEIR USE

(75) Inventors: David Rigal, Frankfurt am Main (DE); Franceska Fischer, Frankfurt am Main (DE); Bernd Becker, Frankfurt am Main (DE); Martin Feth, Frankfurt am Main (DE); Norbert Nagel, Frankfurt am Main (DE); Bruno Baumgartner, Frankfurth am Main (DE); Martin Bröeckelmann, Frankfurt am Main (DE)

(73) Assignee: Sanofi, Paris (FR)

( * ) Notice: Subject to any disclaimer, the term of this patent is extended or adjusted under 35 U.S.C. 154(b) by 254 days.

(21) Appl. No.: 13/391,842

(22) PCT Filed: Aug. 26, 2010

(86) PCT No.: PCT/EP2010/062461
§ 371 (c)(1),
(2), (4) Date: Jun. 5, 2012

(87) PCT Pub. No.: WO2011/023754
PCT Pub. Date: Mar. 3, 2011

(65) Prior Publication Data
US 2012/0238514 A1    Sep. 20, 2012

(30) Foreign Application Priority Data

Aug. 26, 2009  (EP) ..................................... 09290650

(51) Int. Cl.
*C07H 17/02* (2006.01)
*A01N 43/04* (2006.01)
*A61K 31/70* (2006.01)

(52) U.S. Cl.
CPC ...................................... *C07H 17/02* (2013.01)
USPC .......................................... 536/17.4; 514/27

(58) Field of Classification Search
None
See application file for complete search history.

(56) References Cited

U.S. PATENT DOCUMENTS

2007/0197623 A1\*  8/2007  Brummerhop et al. ....... 514/403

FOREIGN PATENT DOCUMENTS

EP          1758914 A1         3/2007
WO    WO2005/121161 A1      12/2005

OTHER PUBLICATIONS

International Preliminary Report on Patentability dated Feb. 28, 2012 issued in PCT/EP2010/062461.
Rye, Carl S. et al., "Elucidation of the Mechanism of Polysaccharide Cleavage by Chondroitin AC Lyase from *Flavobacterium heparinum*," Journal of the American Chemical Society (2002), vol. 124, pp. 9756-9767.
Card, Peter J., "Fluorinated Carbohydrates. Use of (Diethylamino)sulfur Trifluoride in the Synthesis of Fluorinated Sugars," Journal of Organic Chemistry (1983), vol. 48, pp. 393-395.
International Search Report dated Sep. 24, 2010 issued in PCT/EP2010/062461.
European Search Report dated Dec. 21, 2009 issued in EP09290650.

\* cited by examiner

*Primary Examiner* — Layla Bland
(74) *Attorney, Agent, or Firm* — Scully, Scott, Murphy & Presser, P.C.

(57)      ABSTRACT

The invention relates to crystalline hydrates of the formula I

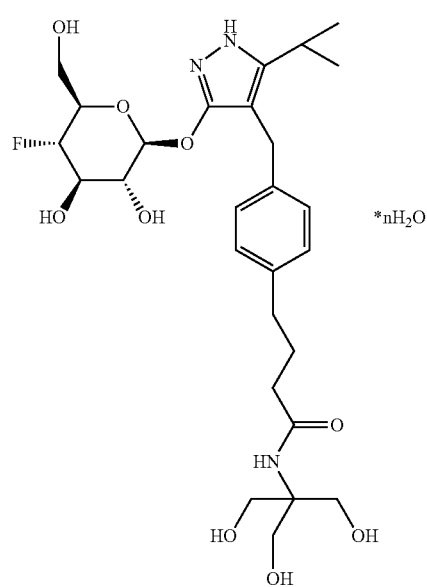

in which n has a value of from 2.1 to 2.5. The compound is suitable, for example, as an antidiabetic.

15 Claims, 12 Drawing Sheets

CRYSTALLINE HETEROAROMATIC FLUOROGLYCOSIDE HYDRATES, PHARMACEUTICALS COMPRISING THESE COMPOUNDS AND THEIR USE

The invention relates to the crystalline hydrates of a heteroaromatic fluoroglycoside.

Amorphous heteroaromatic fluoroglycosides have already been described in EP1758914 B1. One of those heteroaromatic fluoroglycosides is the compound of formula II:

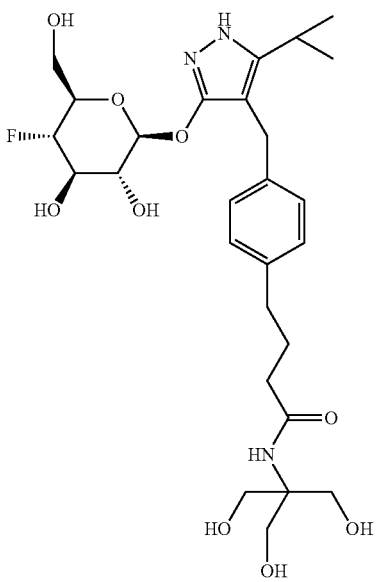

At that time, crystalline hydrates of these fluoroglycosides were not known. It was an object of the invention to provide a heteroaromatic fluoroglycoside which, compared to those described in EP1758914 B1, has improved properties. Another object was to increase the storage stability of the amorphous heteroaromatic fluoroglycoside from EP1758914 B1 which is a crucial parameter for formulating pharmaceuticals.

The object is achieved by providing a crystalline hydrate of the formula I

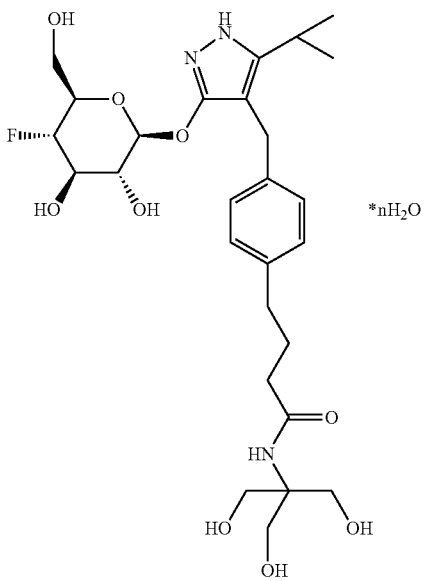

in which n has a value of from 2.1 to 2.5.

Preference is given to the crystalline hydrate of the compound of the formula I in which n has a value of 2.25.

By providing the crystalline hydrates of the formula I according to the invention, the active ingredient

- is easier to purify (for example by recrystallization)
- can have a defined purity required for the approval of a pharmaceutical
- is readily detectable and identifiable by customary methods such as XRPD (X-ray powder diffraction), Raman spectrum, IR (infrared spectrum), and it has
- a reproducible physical quality
- a better chemical stability during storage at 40° C. under dry conditions (closed vials) and 75% r.h (relative humidity).
- is less hygroscopic at 80% r.h. (25° C.) than the amorphous form Crystalline active ingredients are generally more stable than amorphous active ingredients. Problems with the degradation of the active ingredients and the degradation products formed are thus avoided.

The amorphous form of an active ingredient may also comprise an unwanted content of solvents. These are generally difficult to remove, since recrystallization is not possible.

The amorphous form contains more energy than the crystalline form. This may lead to the random pattern of the distribution of the molecules of the amorphous form rearranging spontaneously with release of energy, and partial dissipation of energy. This may result in changes in the activity of the active ingredient without this being directly evident in a measurable parameter of the active ingredient. The consequence is a significant effect on the reliability of the active ingredient and thus a risk for the patient.

It is difficult to prove that different batches of the amorphous active ingredient are identical.

A further embodiment of the invention comprises a crystalline hydrate of the formula I wherein the XRPD, measured with CuKα radiation, has a main peak of 5.8 degrees 2 theta±0.2 degrees 2 theta.

A further embodiment of the invention comprises a crystalline hydrate of the formula I wherein the XRPD, measured with CuKα radiation, has at least peaks of the following 2 theta values:

5.8, 10.3, 14.2±0.2 degrees 2 theta.

A further embodiment of the invention comprises a crystalline hydrate of the formula I wherein the XRPD, measured with CuKα radiation, has at least peaks of the following 2 theta values:

5.8, 7.1, 10.3, 14.2, 19.7±0.2 degrees 2 theta.

A further embodiment of the invention comprises a crystalline hydrate of the formula I wherein the XRPD, measured with CuKα radiation, has at least peaks of the following 2 theta values:

5.8, 7.1, 10.3, 14.2, 19.9, 19.7, 21.8±0.2 degrees 2 theta.

Formulations

The amount of a compound of formula I necessary to achieve the desired biological effect depends on a number of factors, for example the specific compound chosen, the intended use, the mode of administration and the clinical condition of the patient. The daily dose is generally in the range from 0.01 mg to 100 mg (typically from 0.05 mg and 50 mg) per day and per kilogram of body weight, for example 0.05-10 mg/kg/day.

Single-dose formulations which can be administered orally, such as, for example, tablets or capsules may contain, for example, from 1.0 to 1000 mg, typically from 5 from 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. The carrier of solid form is preferred. Other pharmaceutically active substances may likewise be present, including further compounds of the formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral and peroral (for example sublingual) administration, although the most suitable mode of administration depends in each individual case on the nature and severity of the condition to be treated and on the nature of the compound of formula I used in each case. Coated formulations and coated slow-release formulations also belong within the framework of the invention. Acid- and gastric juice-resistant formulations are possible. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Combination with Other Active Ingredients

The compound(s) of the invention (I) can also be administered in combination with further active ingredients.

Further Active Ingredients Suitable for Combination Products Are:

All antidiabetics which are mentioned in the Rote Liste 2007, chapter 12; all weight-reducing agents/appetite suppressants which are mentioned in the Rote Liste 2005, chapter 1; all lipid-lowering agents which are mentioned in the Rote Liste 2007, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or Levemir® (insulin detemir) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-Lyn™ (Generex Biotechnology), GLP-1 derivatives and GLP-1 agonists such as, for example, exenatide, liraglutide or those which have been disclosed in WO98/08871 or WO2005027978, WO2006037811, WO2006037810 of Novo Nordisk A/S, in WO01/04156 of Zealand or in WO00/34331 of Beaufour-Ipsen, pramlintide acetate (Symlin; Amylin Pharmaceuticals), BIM-51077, PC-DAC:exendin-4 (an exendin-4 analog covalently bonded to recombinant human albumin), agonists like those described for example in a Chen et al., Proc. Natl. Acad. Sci. USA 104 (2007) 943, those described in WO2006124529, and orally effective hypoglycemic active ingredients.

Antidiabetics also include agonists of the glucose-dependent insulinotropic polypeptide (GIP) receptor as described for example in WO2006121860.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, pinacidil, cromakalim, diazoxide or those described in R. D. Carr et al., Diabetes 52, 2003, 2513-2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 of Novo Nordisk A/S,
inhibitors, of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption, inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.), or WO2005044256 or WO2005062824 (Merck & Co.) or WO2005061451 and WO2005061452 (AstraZeneca AB), and WO2006017257 (Phenomix) or WO2005033100 (Lipideon Biotechnology AG) or as described in WO2004097655, WO2004000805, WO2004000804, WO2004000803, WO2002050068, WO2002050060, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163.

In one embodiment of the invention, the compound of the formula I is administered in combination with Vytorin™, a fixed combination of ezetimibe with simvastatin.

In one embodiment of the invention, the compound of the formula I is administered in combination with a fixed combination of ezetimibe with atorvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate with rosuvastatin.

In a further embodiment of the invention, the compound of the formula I is administered in combination with synordia (R), a fixed combination of fenofibrate with metformin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with Competact™, a fixed combination of pioglitazone hydrochloride with metformin hydrochloride.

In one embodiment of the invention, the compound of the formula I is administered in combination with Tandemact™, a fixed combination of pioglitazone with glimepride.

In a further embodiment of the invention, the compound of the formula I is administered in combination with a fixed combination of pioglitazone hydrochloride with an angiotensin II agonist such as, for example, TAK-536.

In one embodiment of the invention, the compound of the formula I is administered in combination with a PPAR alpha agonist such as, for example, GW9578, GW-590735, K-111, LY-674, KRP-101, DRF-10945, LY-518674 or those described in WO2001040207, WO2002096894, WO2005097076.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, CKD-501 (lobeglitazone sulfate) or as described in WO 00/64888, WO 00/64876, WO 03/020269 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516 or as described in WO2006059744, WO2006084176, WO2006029699, WO2007039172, WO2007039178.

In one embodiment, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757, AS-1552133 or those described in WO2005085226, WO2005121091, WO2006010423.

In one embodiment of the invention, the compound of the formula I is administered in combination with a CETP inhibitor such as, for example, torcetrapib or JTT-705 or those described in WO2006002342, WO2006010422, WO2006012093, WO2006073973, WO2006072362, WO2006097169, WO2007041494.

In one embodiment of the invention, the compound of the formula I is administered in combination with a bile acid absorption inhibitor (see, for example, U.S. Pat. No. 6,245,744, U.S. Pat. No. 6,221,897 or WO00/61568), such as, for example, HMR 1741 or those as described in DE 10 2005 033099.1 and DE 10 2005 033100.9, WO2007009655-56.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment of the invention, the compound of the formula I is administered in combination with an ABCA1 expression enhancer as described for example in WO2006072393.

In a further embodiment of the invention, the compound of the formula I is administered in combination with an RNAi therapeutic directed against PCSK9 (proprotein convertase subtilisin/kexin type 9).

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494, TAK-475 or as described in WO2005077907, JP2007022943.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist; NAR agonist (nicotinic acid receptor agonist) such as, for example, nicotinic acid or extended release niacin in conjunction with MK-0524A or the compounds described in WO2006045565, WO2006045564, WO2006069242, WO2006124490, WO2006113150, WO2007017261, WO2007017262, WO2007017265, WO2007015744, WO2007027532.

In another embodiment of the invention, the compound of the formula I is administered in combination with an agonist of GPR116 as described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide or glimepiride.

In one embodiment, the compound of the formula I is administered in combination with a substance which enhances insulin secretion, such as, for example, KCP-265 (WO2003097064) or those described in WO2007026761.

In one embodiment, the compound of the formula I is administered in combination with agonists of the glucose-dependent insulinotropic receptor (GDIR), such as, for example, APD-668.

In one embodiment, the compound of the formula I is administered in combination with a biguanide such as, for example, metformin.

In another embodiment, the compound of the formula I is administered in combination with a meglitinide such as, for example, repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment, the compound of the formula I is administered in combination with glucagon receptor antagonists such as, for example, A-770077, NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described for example in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515, WO2006104030, WO2007014619.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment, the compound of the formula I is administered in combination with inhibitors of dipeptidylpeptidase IV (DPP-IV), such as, for example, vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200, GW-825964X, KRP-104, DP-893, ABT-341, ABT-279 or another salt thereof, or the compounds described in WO2003074500, WO2003106456, WO2004037169, WO200450658, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006090915, WO2006104356, WO2006127530, WO2006111261, WO2007015767, WO2007024993, WO2007029086.

In one embodiment, the compound of the formula I is administered in combination with Janumet™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, WO2007051810.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, WO2005116003, WO2006007959, DE 10 2004 060542.4, WO2007009911, WO2007028145, WO2007081755.

In one embodiment, the compound of the formula I is administered in combination with modulators of the sodium-dependent glucose transporter 1 or 2 (SGLT1, SGLT2), such as, for example, KGA-2727, T-1095, SGL-0010, AVE 2268, SAR 7226 and sergliflozin or as are described for example in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170 or by A. L. H and Ion in Expert Opin. Ther. Patents (2005) 15(11), 1531-1540.

In one embodiment, the compound of the formula I is administered in combination with modulators of GPR40 as described for example in WO2007013689, WO2007033002.

In one embodiment, the compound of the formula I is administered in combination with modulators of GPR119b as described for example in WO2004041274.

In one embodiment, the compound of the formula I is administered in combination with modulators of GPR119 as described for example in WO2005061489 (PSN-632408), WO2004065380, WO2007003960-62 and WO2007003964.

In a further embodiment, the compound of the formula I is administered in combination with modulators of GPR120.

In one embodiment, the compound of the formula I is administered in combination with inhibitors of hormone-sensitive lipase (HSL) and/or phospholipases as described for example in WO2005073199, WO2006074957, WO2006087309, WO2006111321, WO2007042178.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559, WO2007011809, WO2007011811, WO2007013691.

In a further embodiment, the compound of the formula I is administered in combination with modulators of xanthine oxidoreductase (XOR).

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase 3 beta (GSK-3 beta), as described for example in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, the compound of the formula I is administered in combination with an inhibitor of the serum/glucocorticoid-regulated kinase (SGK) as described for example in WO2006072354.

In one embodiment, the compound of the formula I is administered in combination with an agonist of the RUP3 receptor as described for example in WO2007035355.

In one embodiment, the compound of the formula I is administered in combination with an inhibitor of protein kinase C beta (PKC beta), such as, for example, ruboxistaurin.

In another embodiment, the compound of the formula I is administered in combination with an activator of the gene which codes for the ataxia telangiectasia mutated (ATM) protein kinase, such as, for example, chloroquine.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor (GR), like those described for example in WO2005090336, WO2006071609, WO2006135826.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-aminoquinazolin-2-ylamino)methyl] cyclohexylmethyl}amide hydrochloride (CGP 71683A);

NPY-5 receptor antagonists such as L-152804 or such as described, for example, in WO2006001318;

NPY-4 receptor antagonists such as described, for example, in WO2007038942;

NPY-2 receptor antagonists such as described, for example, in WO2007038943;

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424, WO2006095166; derivatives of the peptide obestatin such as those described in WO2006096847;

CB1R (cannabinoid receptor 1) antagonists (such as, for example, rimonabant, SR147778, SLV-319, AVE-1625, MK-0364 or salts thereof or compounds such as those described for example in EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067480, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737, WO2007084319, WO2007084450);

cannabinoid receptor 1/cannabinoid receptor 2 (CB1/CB2) modulating compounds as described for example in WO2007001939, WO2007044215, WO2007047737; MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide, (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458, WO2006067224);

histamine H3 receptor agonists (e.g. 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893, WO2006107661, WO2007003804, WO2007016496, WO2007020213);

histamine H1/histamine H3 modulators such as, for example, betahistine or its dihydrochloride;

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as are described in JP2006111553, WO2002038543, WO2007048840-843;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180) or those as are described in WO2005116034;

serotonin reuptake inhibitors (e.g. dexfenfluramine);

mixed serotonin/dopamine reuptake inhibitors (e.g. bupropion) or fixed combinations of bupropion with naltrexone;

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

mixed dopamine/norepinephrine/acetylcholine reuptake inhibitors (e.g. tesofensine);

5-HT2C receptor agonists (such as, for example, lorcaserin hydrochloride (APD-356) or BVT-933 or those as are described in WO200077010, WO200077001-02, WO2005019180, WO2003064423, WO200242304, WO2005035533, WO2005082859, WO2006077025, WO2006103511);

5-HT6 receptor modulators such as, for example E-6837 or BVT-74316 or those as are described in WO2005058858, WO2007054257;
bombesin receptor agonists (BRS-3 agonists);
galanin receptor antagonists;
growth hormone (e.g. human growth hormone or AOD-9604);
growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));
growth hormone secretagogue receptor antagonists (ghrelin antagonists) such as, for example, A-778193 or those as are described in WO2005030734;
TRH agonists (see, for example, EP 0 462 884);
uncoupling protein 2 or 3 modulators;
leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);
DA agonists (bromocriptine or Doprexin);
lipase/amylase inhibitors (for example WO 00/40569);
inhibitors of diacylglycerol O-acyltransferases (DGATs) such as for example BAY-74-4113 or as described for example in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538;
inhibitors of fatty acid synthase (FAS) such as, for example, C75 or those as described in WO2004005277;
inhibitors of stearoyl-CoA delta9 desaturase (SCD1) as described for example in WO2007009236, WO2007044085, WO2007046867, WO2007046868, WO20070501124;
oxyntomodulin;
oleoyl-estrone
or thyroid hormone receptor agonists or partial agonists such as, for example: KB-2115 or those as described in WO20058279, WO200172692, WO200194293, WO2003084915, WO2004018421, WO2005092316, WO2007003419, WO2007009913, WO2007039125.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

FM-VP4

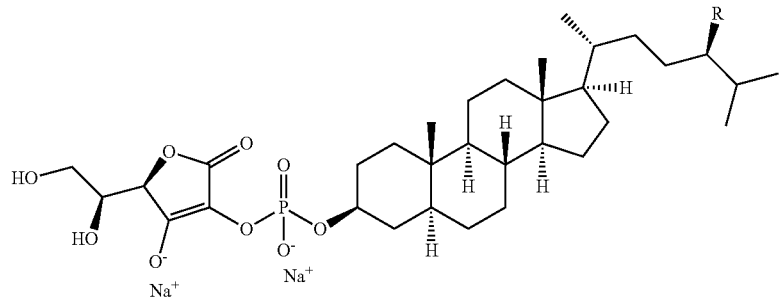

R = CH₃; CH₂—CH₃

JTT-501
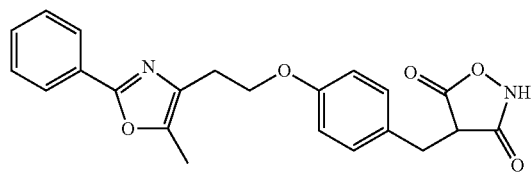
GI 262570
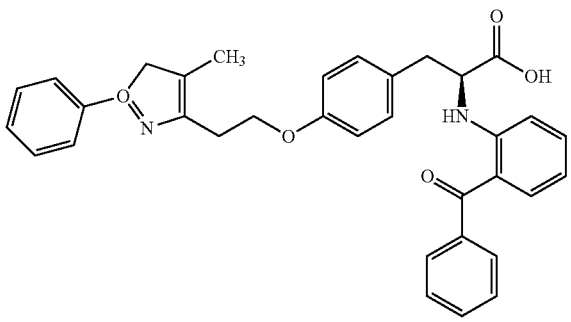
CS-011
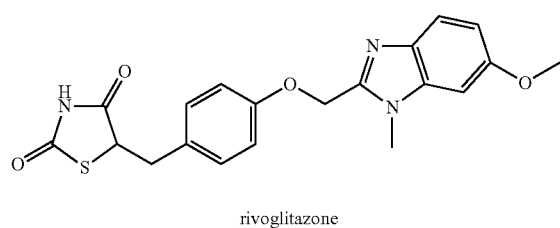
rivoglitazone
GW-9578
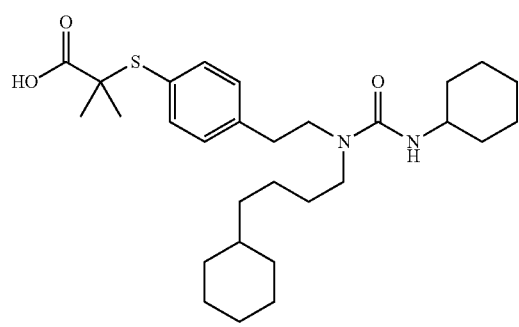
K-111
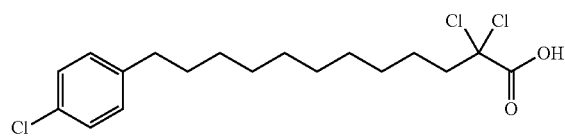
LY-674
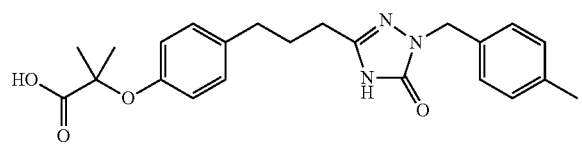
KRP-101
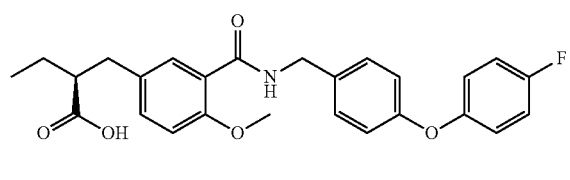
LY-510929
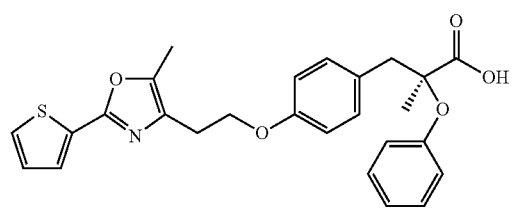
GW-501516
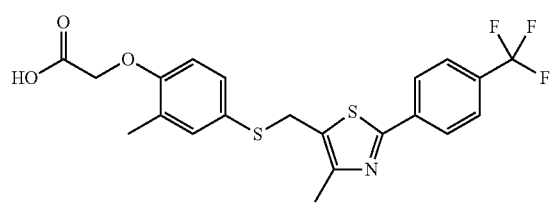
BMS-201038
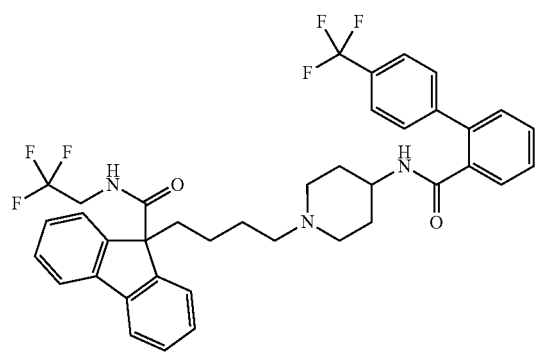

R-103757
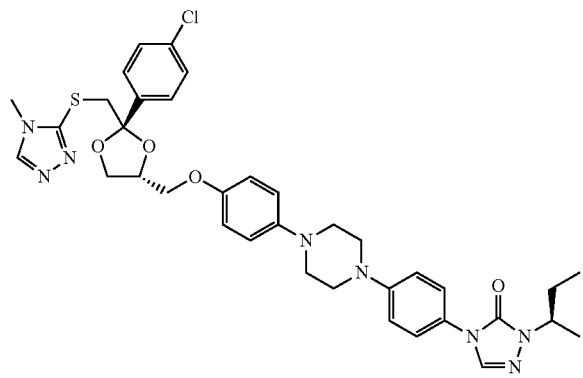
JTT-705
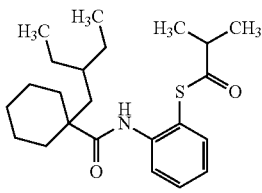
OPC-14117
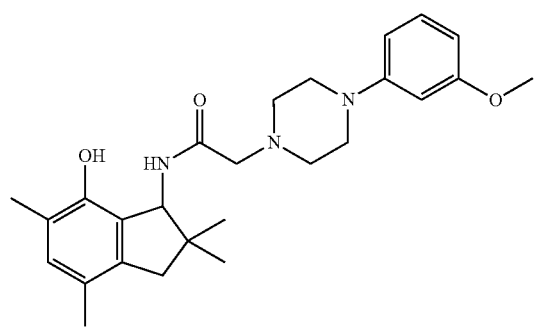
NO-1886
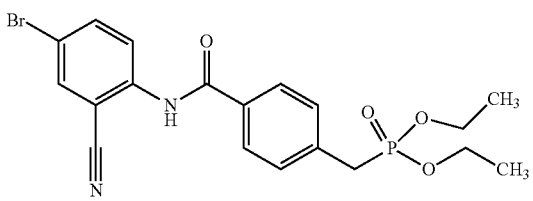
SB-204990
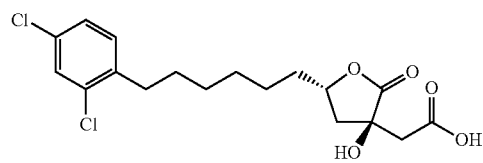
BMS-188494
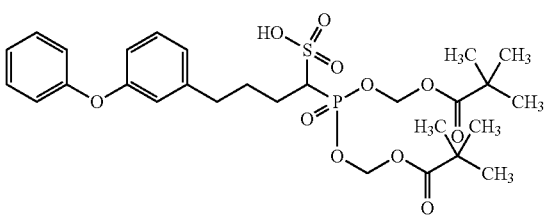
CI-1027
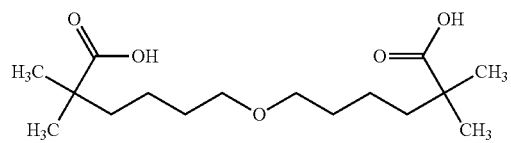
ATL-962
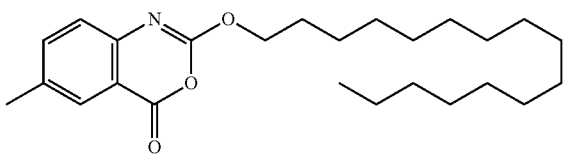
FR-258900
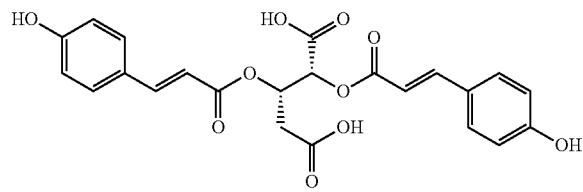
NCC-25-2504
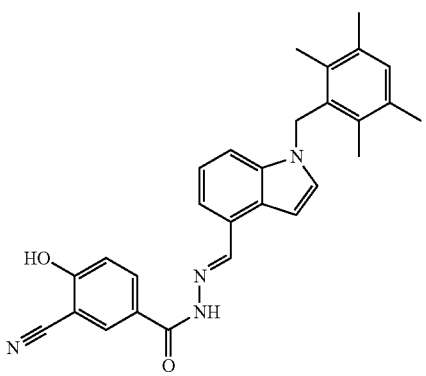

-continued
LY-2121260
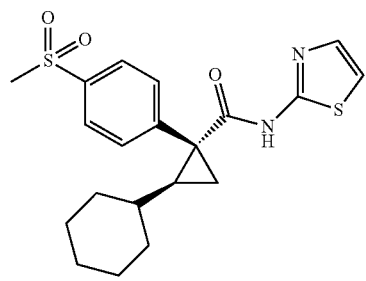
GKA-50
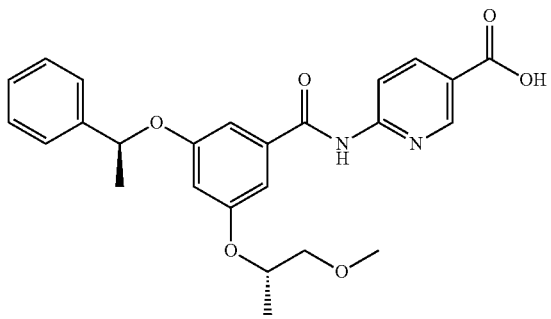
FR-225654
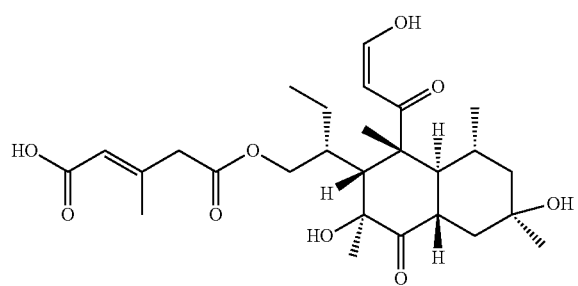
KST-48
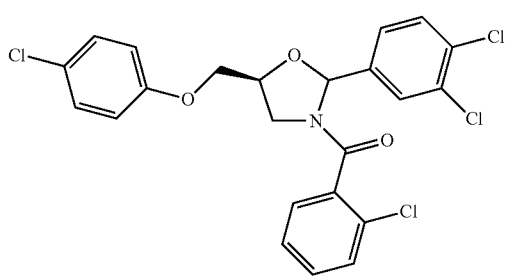
BMS-477118
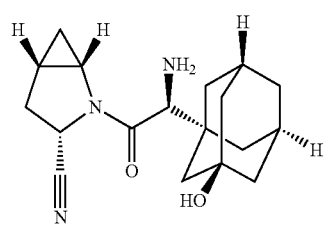
BVT-2733
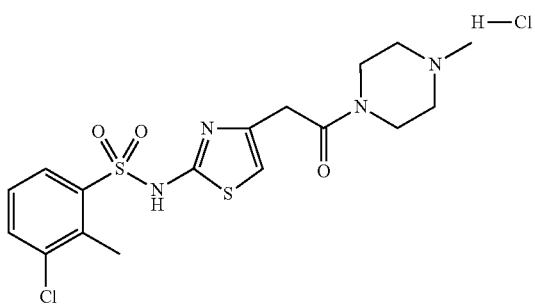
T-1095
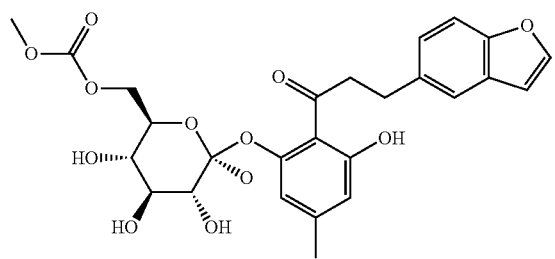
SPP-301
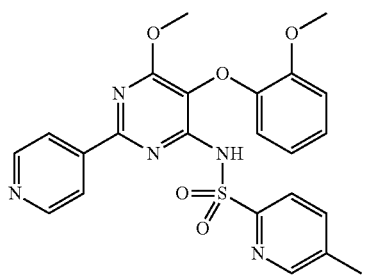

21 22
-continued
THIQ 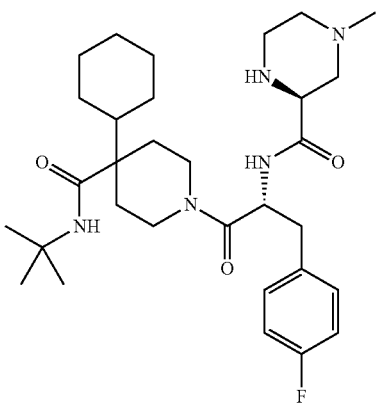 MB243
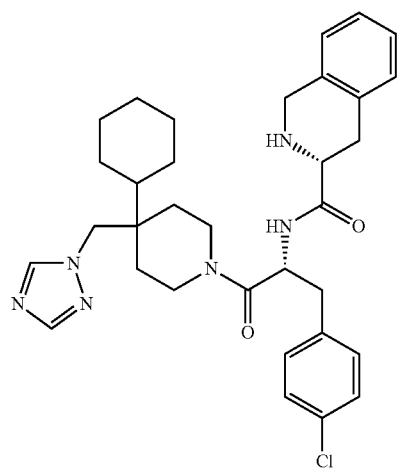
RY764 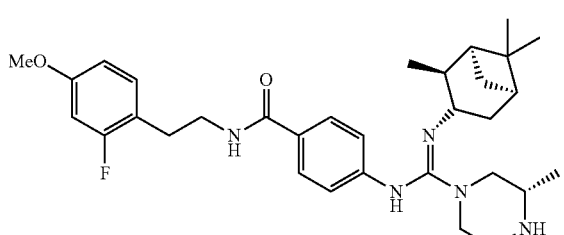 CHIR-785
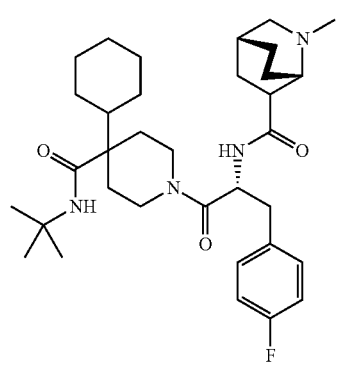
A-761 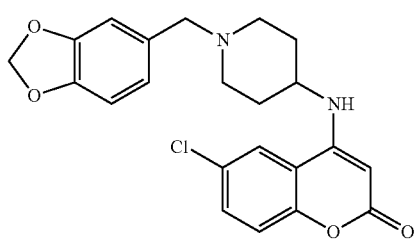 A-665798
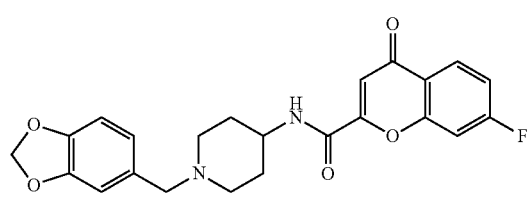
ATC-0175 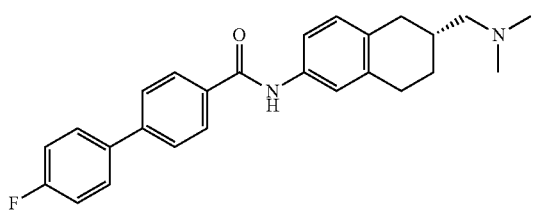 T-226296
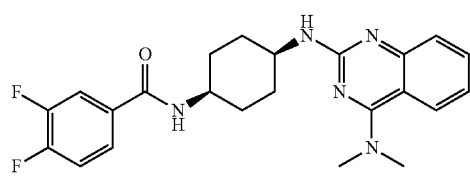
GW-803430
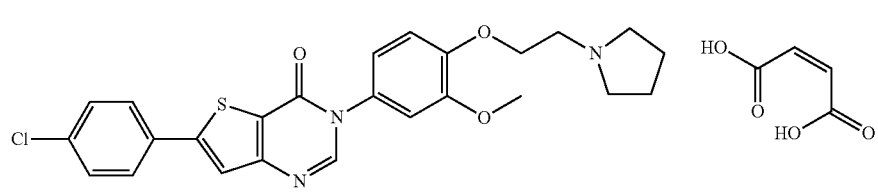

-continued
AOD-9604
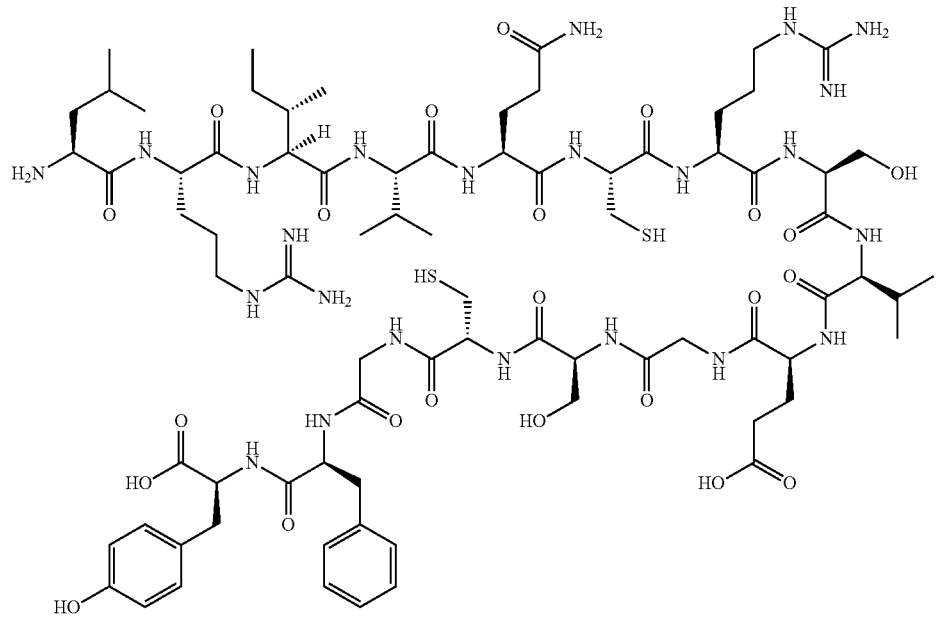
A-778193
C75
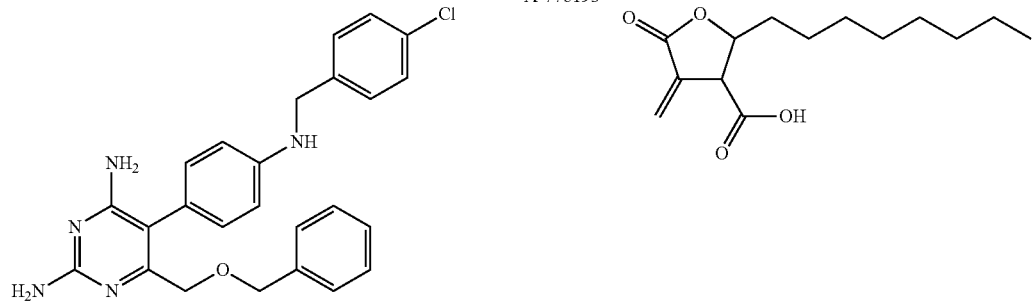
oleoyl-estrone
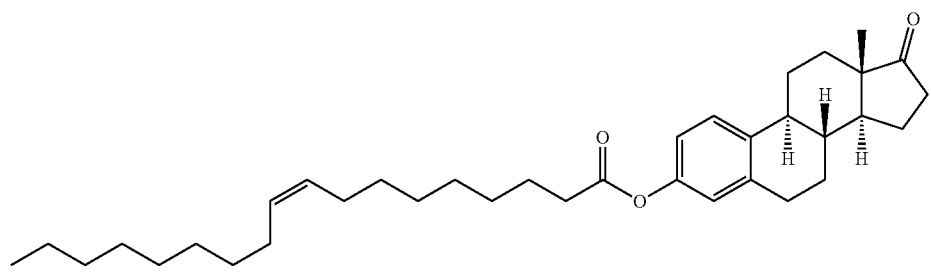
KB-2115
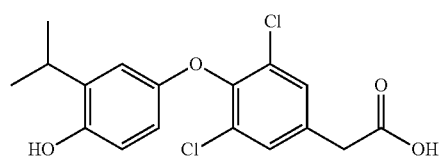
KCP-265
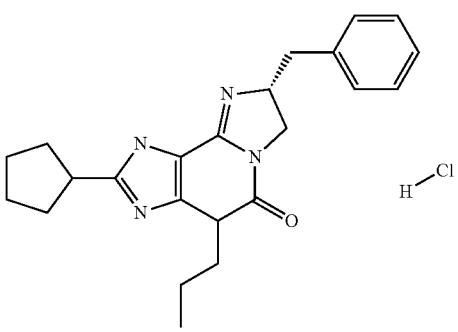

-continued
SMP-797
JNJ-25918646
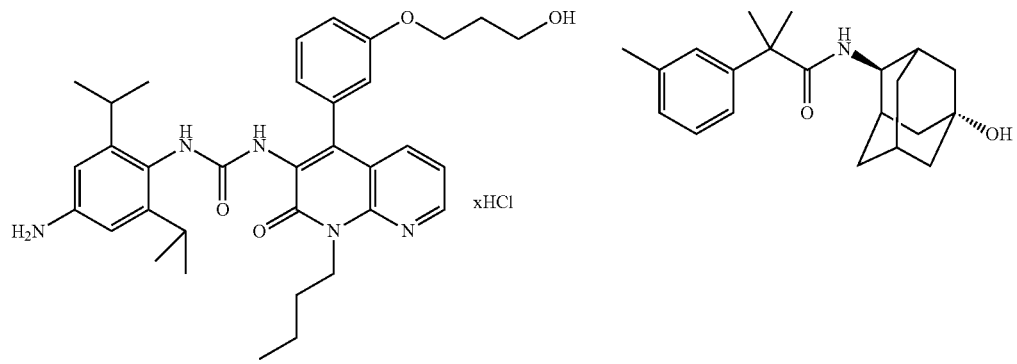
PSN-632408
SYR-322
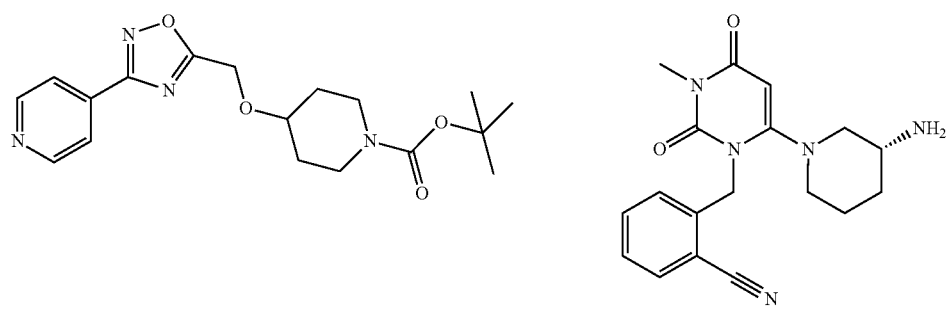
DP-893
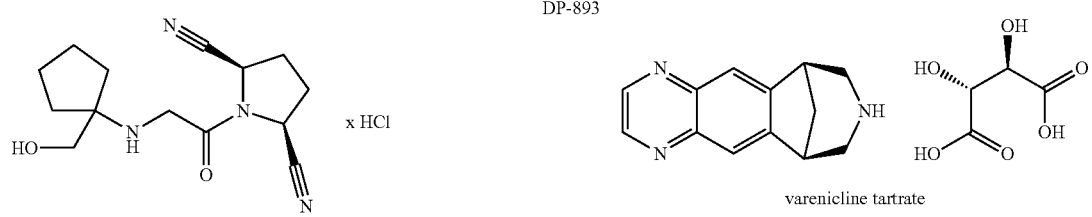
varenicline tartrate
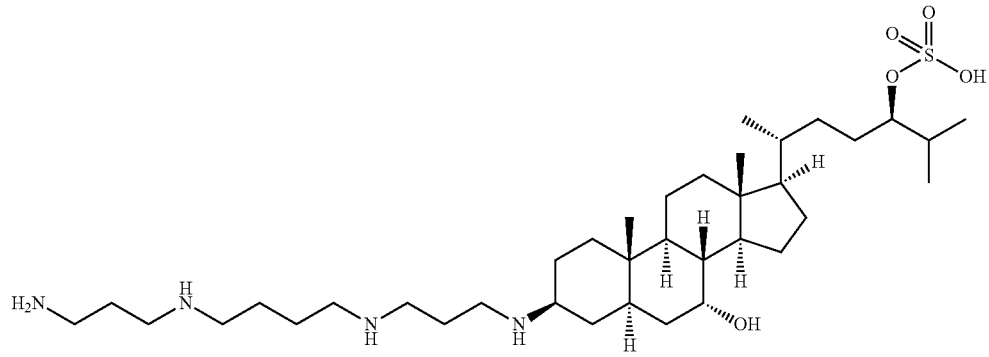
trodusquemine
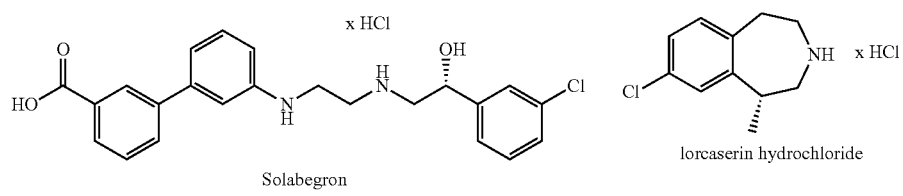
Solabegron
lorcaserin hydrochloride -continued
L-152804
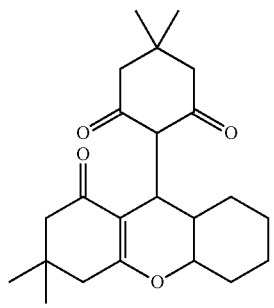
MB-06322
CS-917
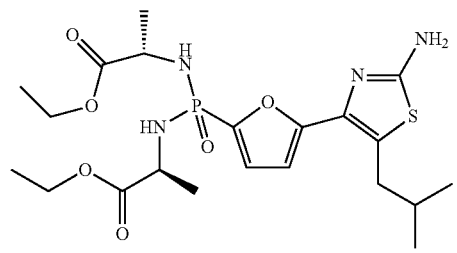
N-5984
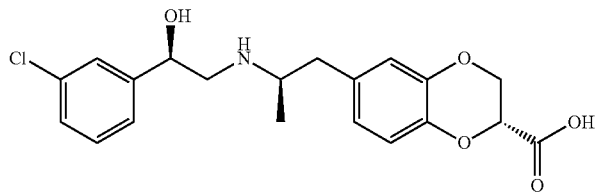
BIM-51077
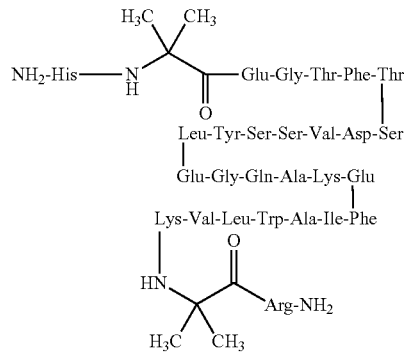
TAK-536
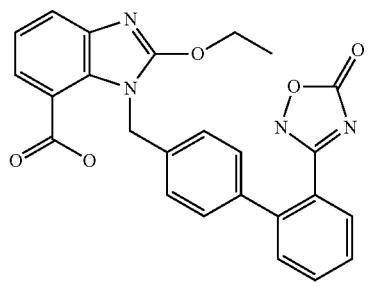
E-6837
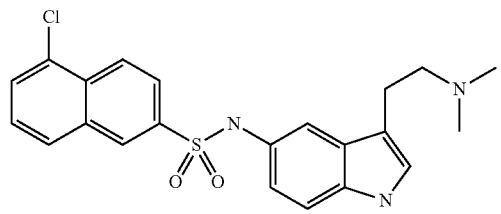
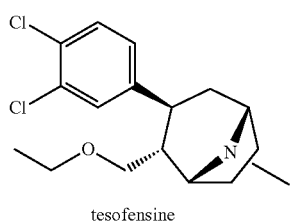
tesofensine
BVT-74316
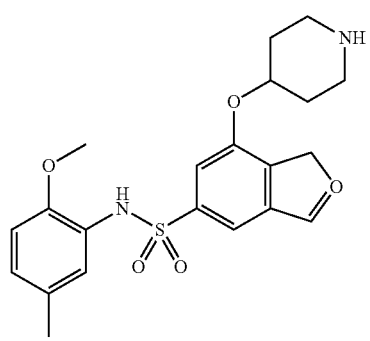
ABT-341
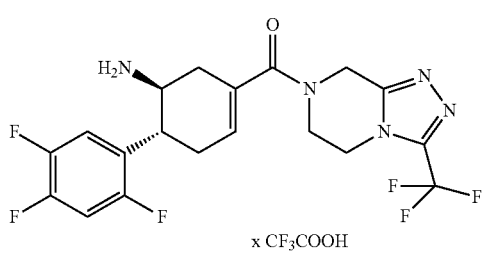
x CF₃COOH
MK-0364
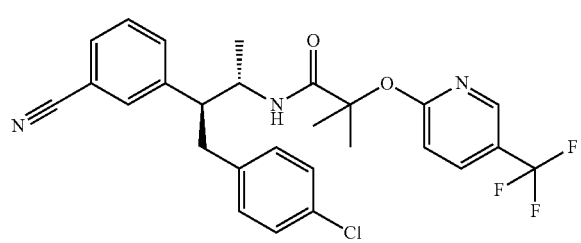

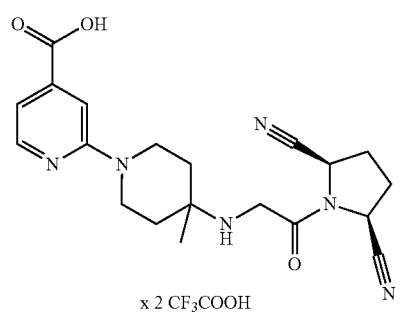
x 2 CF₃COOH
ABT-279
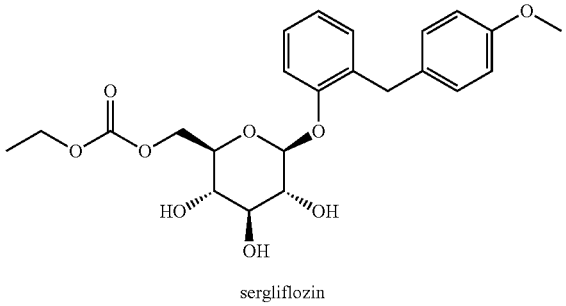
sergliflozin
SLV-319
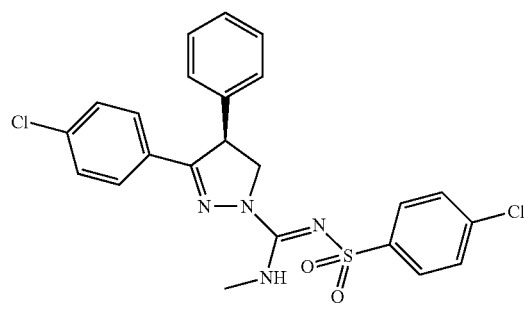
AVE 1625
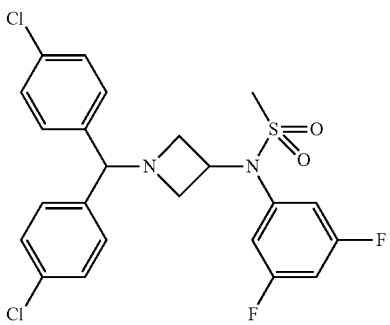
TAK-475
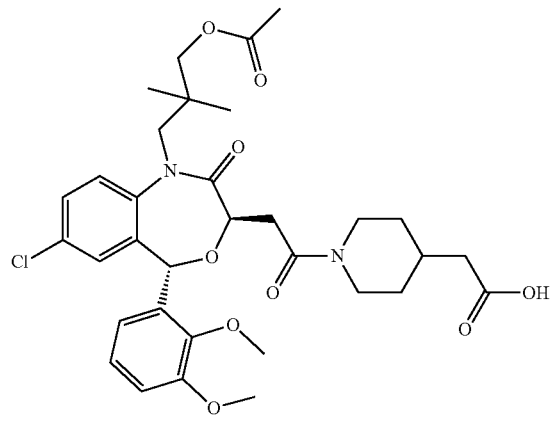
AS-1552133
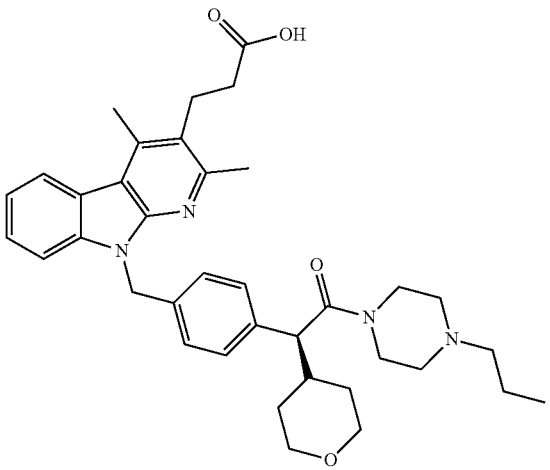
CKD-501
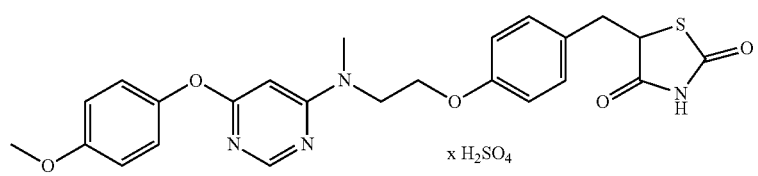
(lobeglitazone sulphate)

Preparation Process

The invention furthermore relates to processes for preparing the compound of the formula I.

EXAMPLE 1A

Crystallisation by Slow Cooling and Seeding of an Aqueous Solution

Concentrated solutions of compound of formula II in water were cooled down from 33° C. to 27° C. within 1 hour and seeded at 27° C. with 0.1 w/w-% hydrate form of compound of formula I. The seeded solution was then cooled to 19° C. during 4 hours. The white product was isolated by filtration and washed with ice-cold purified water. The wet product was statically dried at 24° C. under vacuum and increased humidity ($N_2$ gas stream present) in a vacuum tray drier.

If not stated differently, the crystallization experiments were performed with crude 4-{4-[3-((2S,3R,4R,5S,6R)-5-Fluoro-3,4-dihydroxy-6-hydroxymethyl-tetrahydro-pyran-2-yloxy)-5-isopropyl-1H-pyrazol-4-ylmethyl]-phenyl}-N-(2-hydroxy-1,1-bis-hydroxymethyl-ethyl)-butyramide (HPLC purity>=80%)

Origin of Seeding Crystals

The crystalline hydrate of formula I was first obtained during a freeze-drying experiment of an aqueous solution of compound of formula II.

Crystalline hydrate form was alternatively obtained by spontaneous crystallisation of an aqueous solution of compound of formula II.

The crystalline products of these experiments were consecutively used as seeding crystals for the seeded crystallisation of the crystalline hydrate in water as described in example 1a.

The crystalline hydrate of formula I can be mechanically milled by keeping its crystalline hydrate form by applying cryogenic conditions during the process.

The Crystalline Compound of the Formula I was Characterized by the Following Methods The compound of the formula I obtained exhibits the XRPD shown in FIG. 1. The XRPD was measured in transmission with Cu-Kalpha1 radiation at room temperature.

The most important 2 theta values are summarized in table 1.

TABLE 1

| 2 theta (+/−0.2 degrees 2 theta) |
|---|
| 5.8 |
| 7.1 |
| 10.3 |
| 14.2 |
| 19.7 |
| 19.9 |
| 21.8 |

Owing to natural deviations in the samples or in the measuring method, the 2 theta values of the peaks can be stated with an accuracy of ±0.2 degrees theta.

Figure 1:
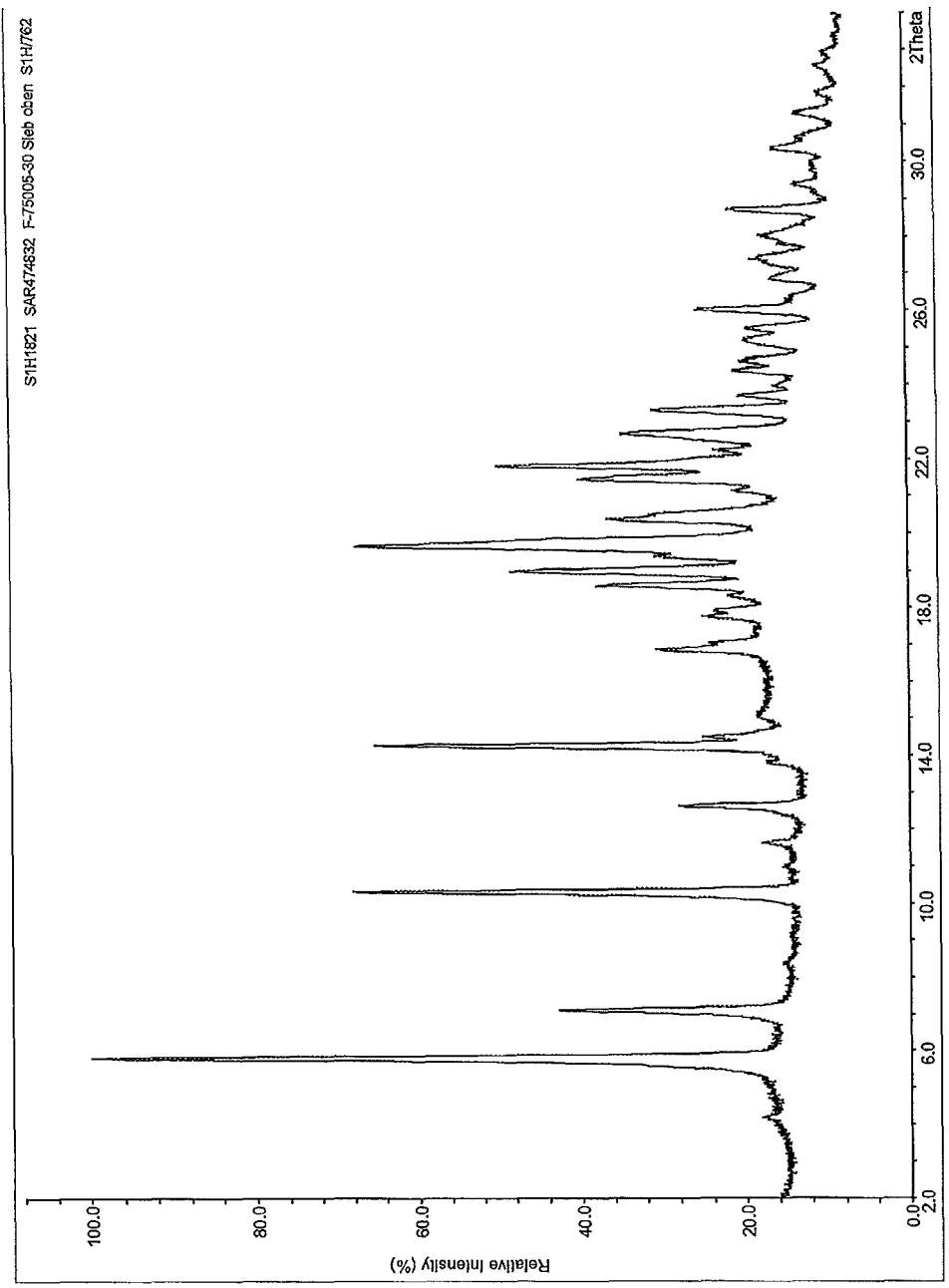
Figure 2:
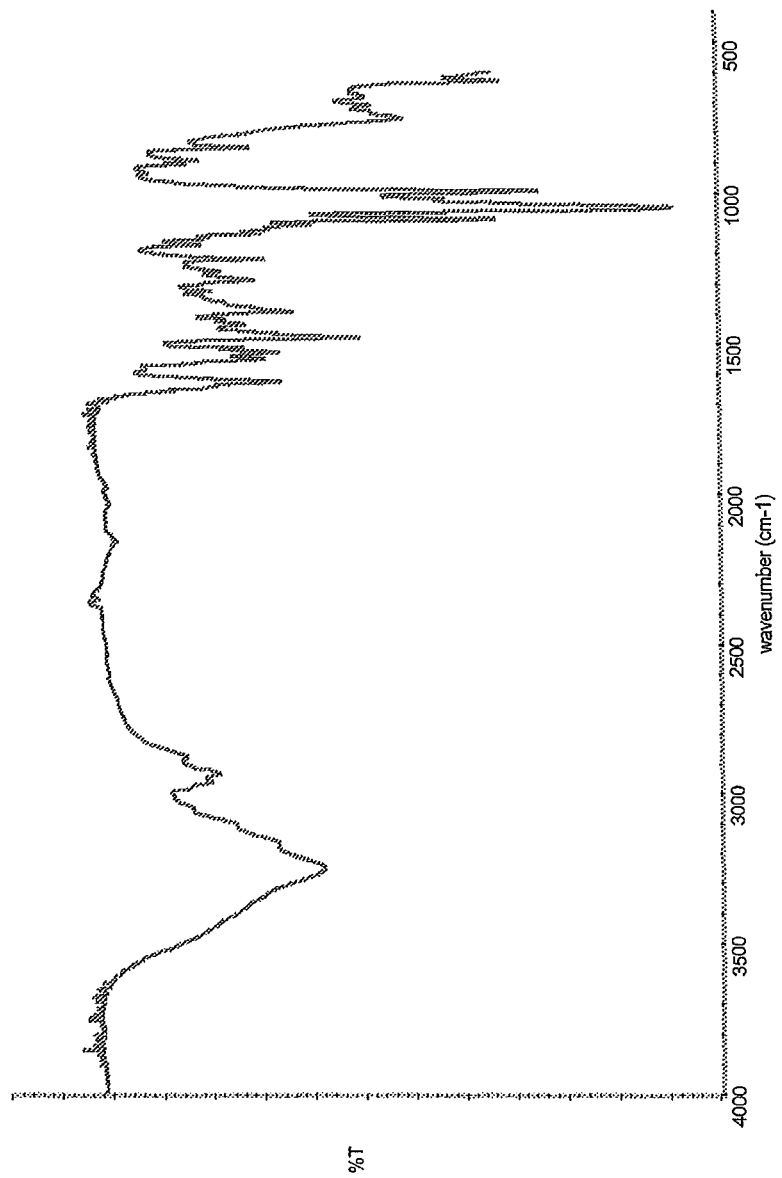
FIG. 2 shows the IR spectrum of the crystalline compound of the formula I
Figure 3:
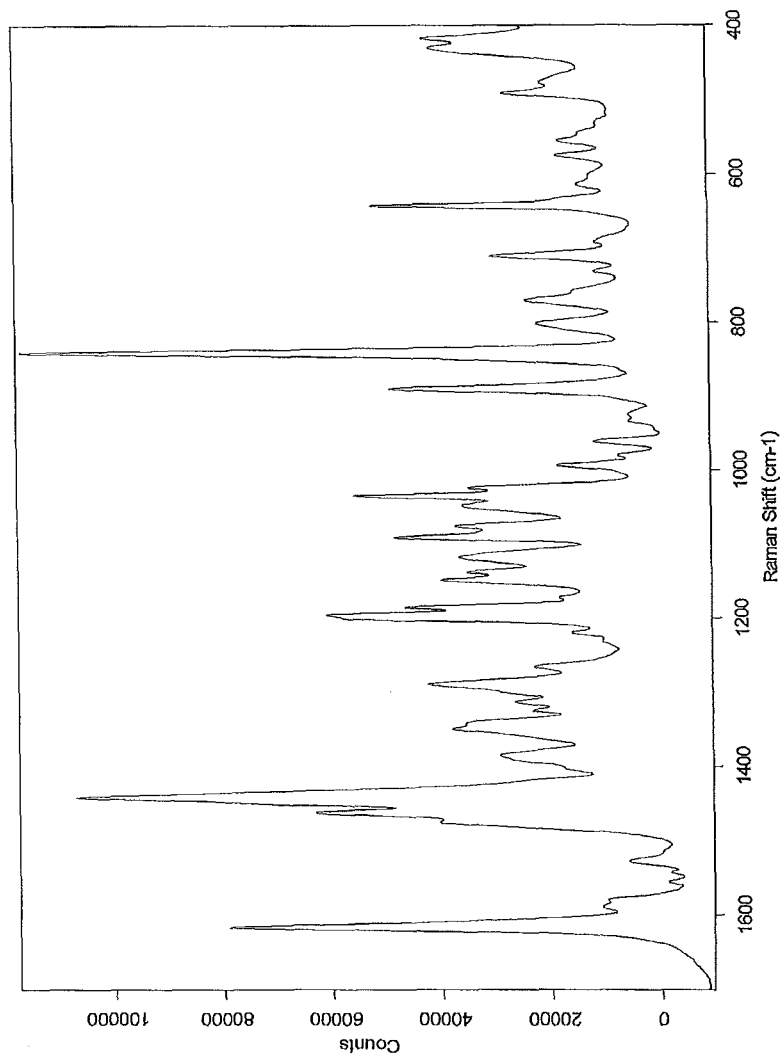
FIG. 3 shows the Raman spectrum of the crystalline compound of the formula I
Figure 4:
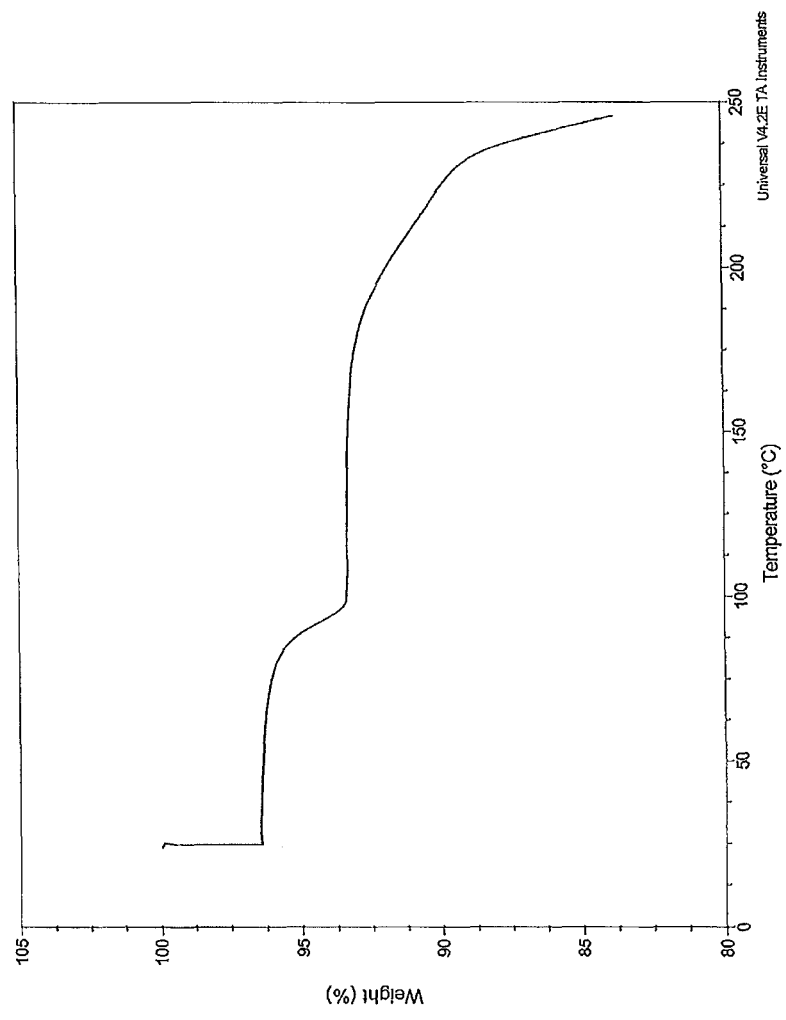
FIG. 4 shows the TGA curve of the crystalline compound of the formula I
Figure 5:
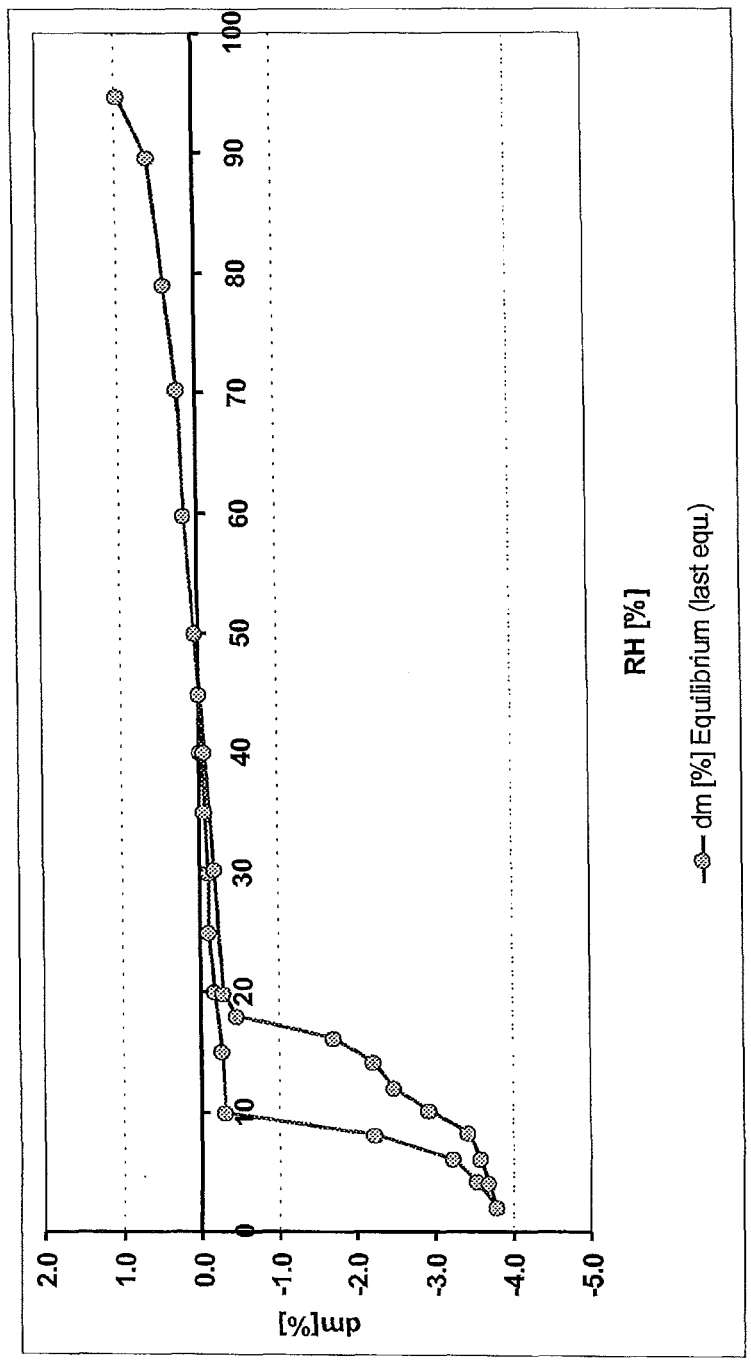
Figure 6:
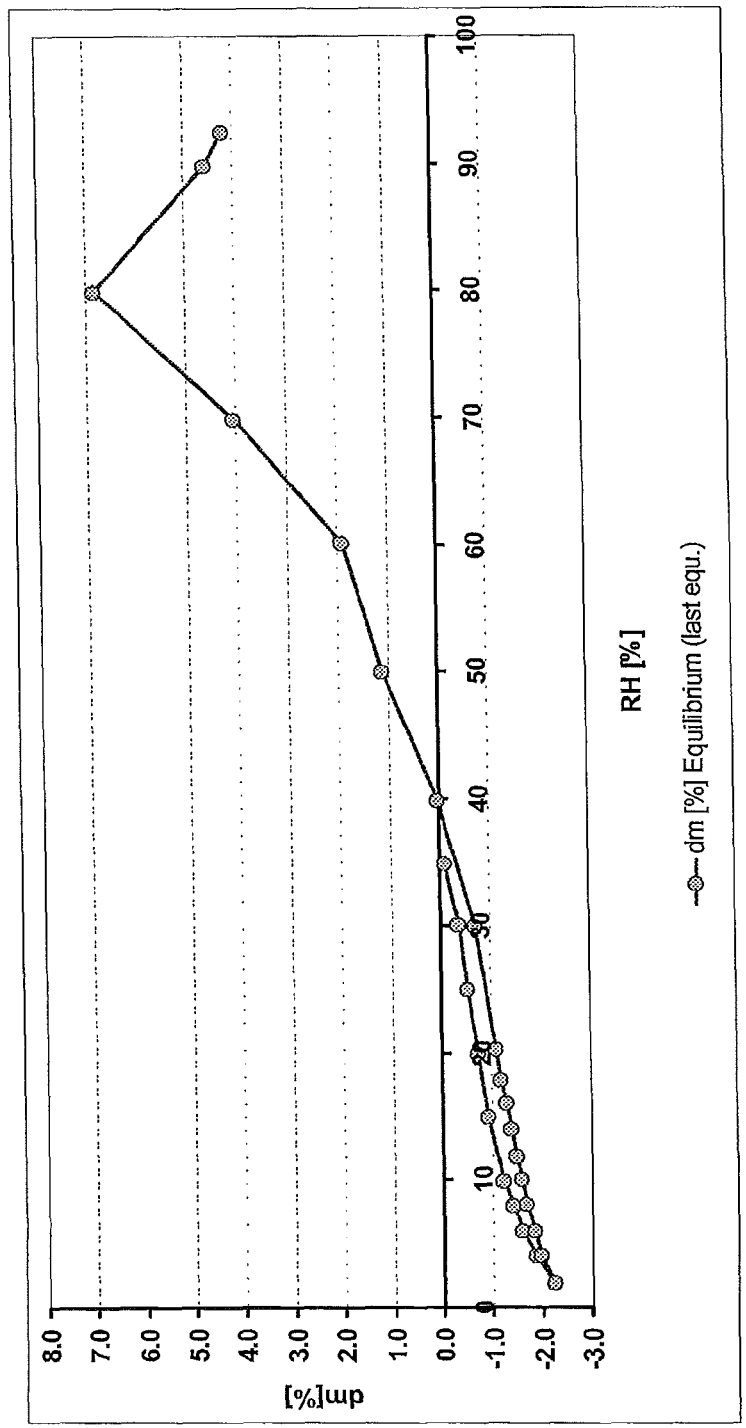
Figure 7:
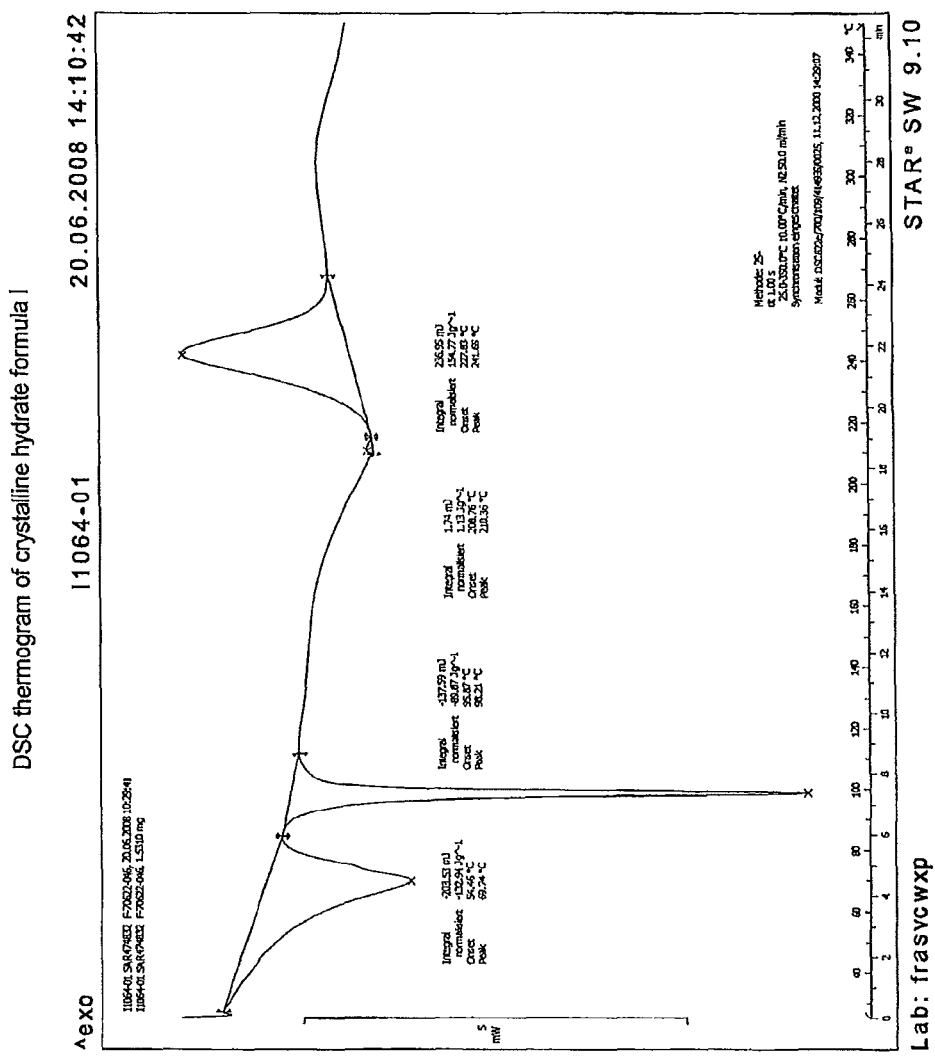
Figure 8:
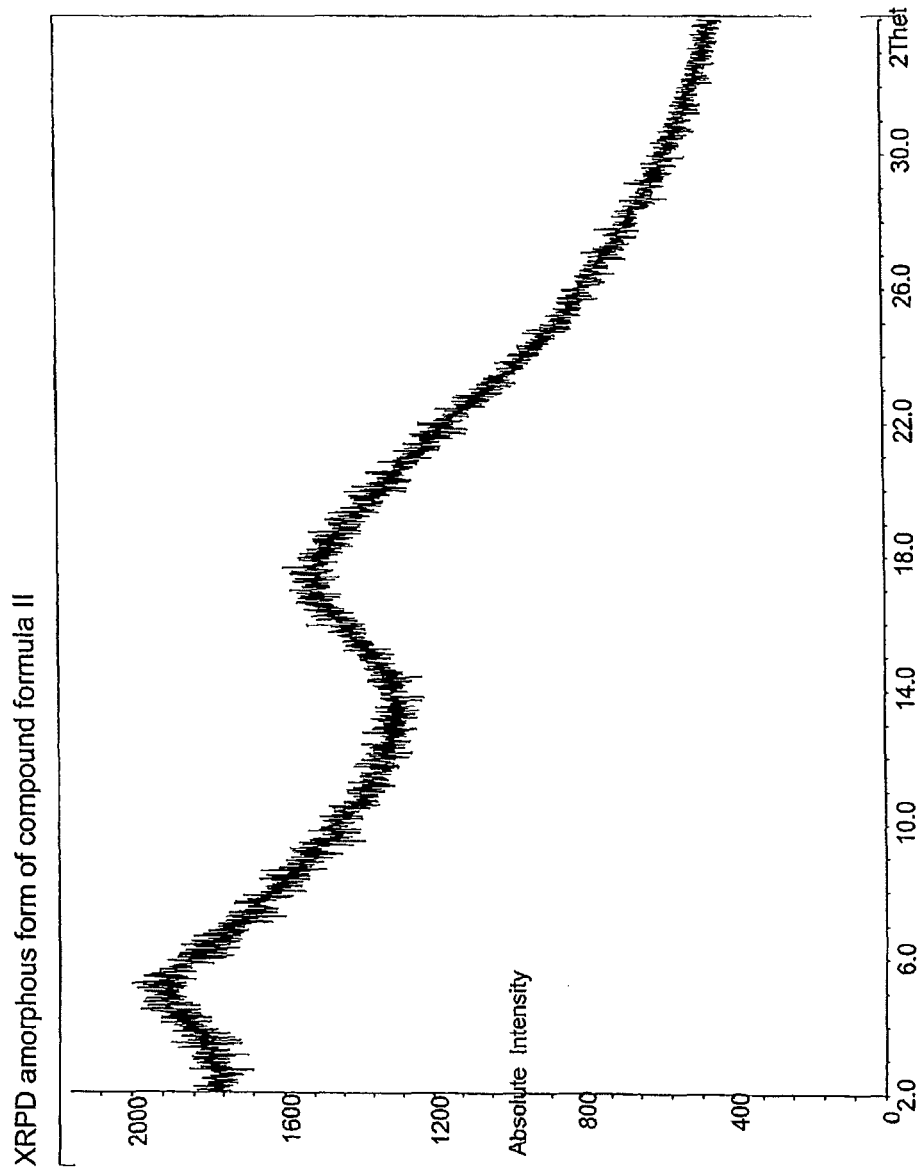
Figure 9:
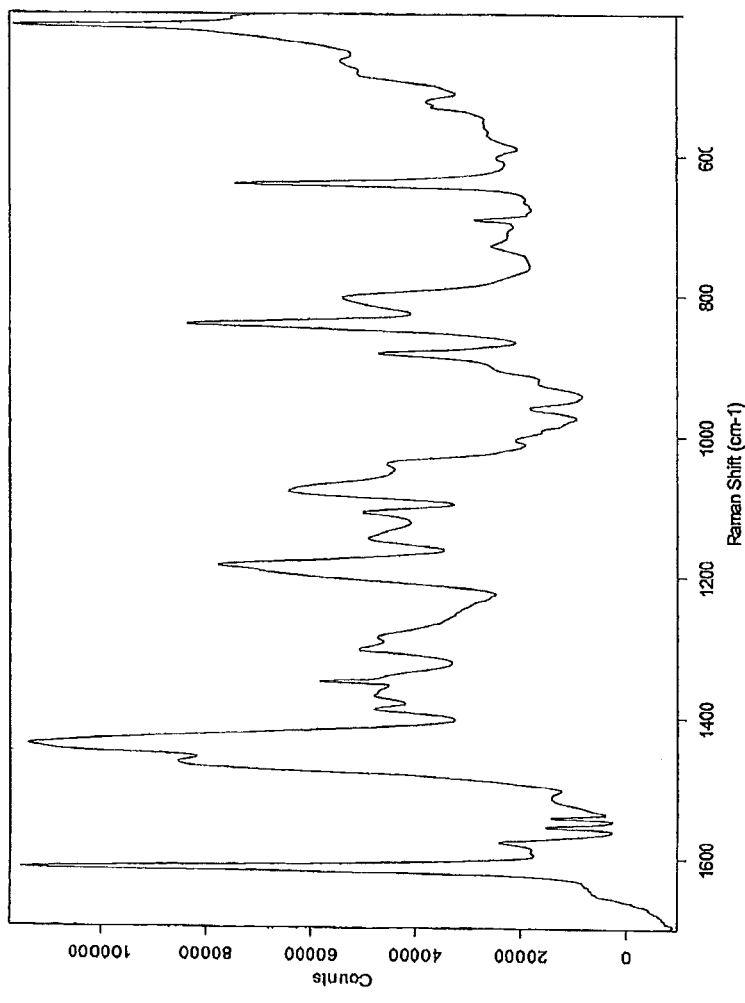
Figure 10:
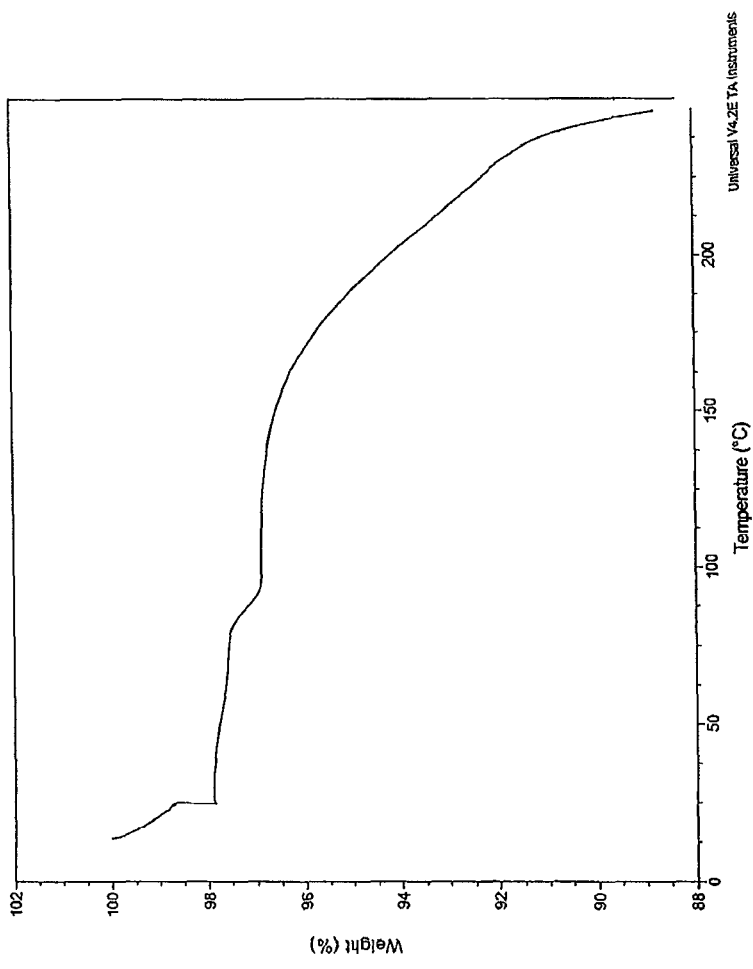
Figure 11:
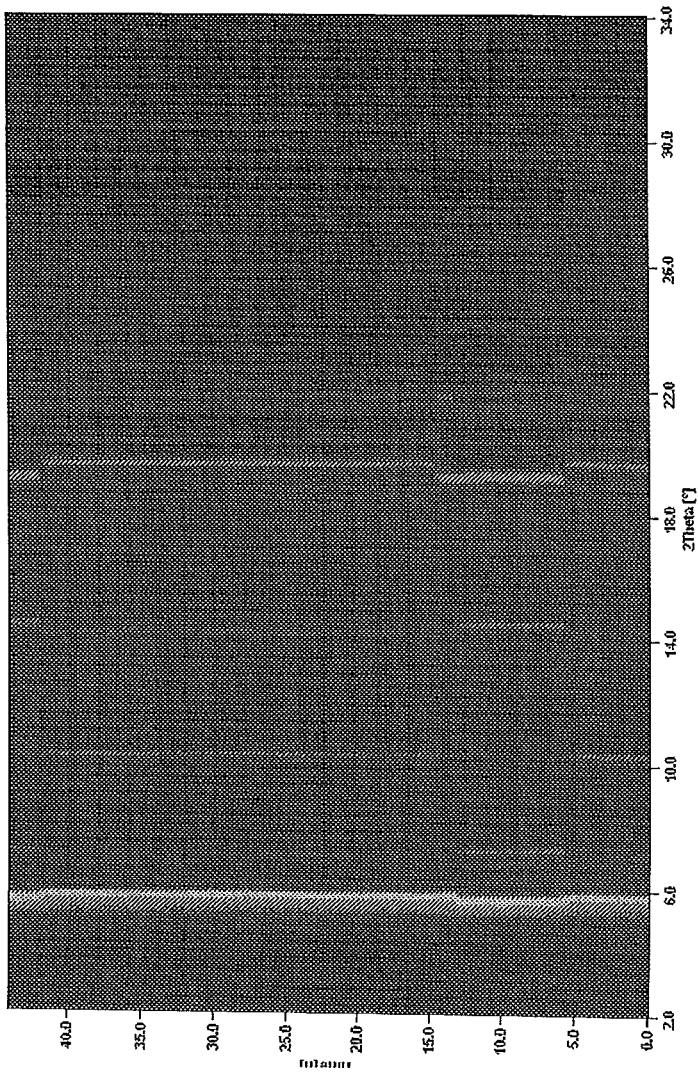
Figure 12:
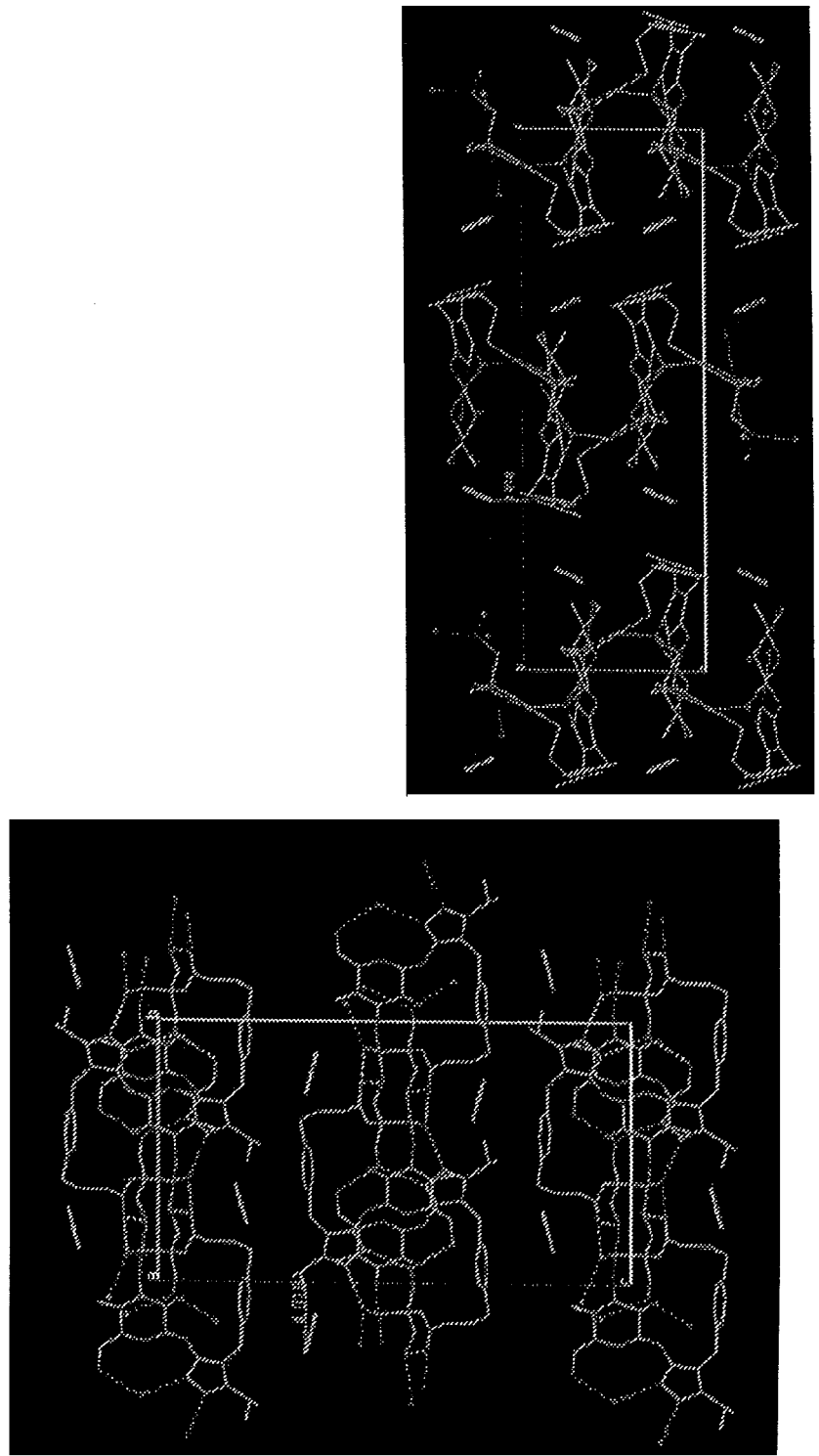

FIG. 5 shows the DVS water vapour sorption and desorption isotherms of the crystalline compound of the formula I FIG. 6 shows the DVS water vapour sorption and desorption isotherms of the X-ray amorphous compound of the formula II FIG. 7 shows the DSC thermogram of the crystalline compound of the formula I FIG. 8 shows the XRPD analysis of the amorphous compound of the formula II FIG. 9 shows the Raman spectrum of the amorphous compound of the formula II FIG. 10 shows the TGA curve of the amorphous compound of the formula II FIG. 11 shows XRPD diagrams as a function of relative humidity at 25° C. for crystalline hydrate formula I FIG. 12 shows crystal packaging of the acetonitrile solvate Analytical Methods and Operation Conditions X-Ray Powder Diffraction (XRPD)

All X-ray powder diffraction was performed with Stoe Stadi-P transmission diffractometers using $CuK_{\alpha 1}$ radiation. Linear position sensitive detectors were used, and unless stated otherwise, X-ray powder diffraction was performed at room temperature. The samples were investigated in a flat preparation. The measured data were evaluated and plotted with the Software WinXPOW V1.1.

Differential Scanning Calorimetry (DSC)

The DSC measurements were performed with a Mettler DSC822e (module DSC822e/700/109/414935/0025) and 40 µl Al crucibles with sealed lid and hole were used. All measurements were carried out in a nitrogen gas flow of 50 mL/minute. The heating rate was 10° C./minute. Temperature and heat flow were calibrated via the melting peak of an indium reference. The measured data were evaluated with the software STARe V6.1.

FT-IR Spectroscopy

Infra-red absorption spectra are recorded on a FT-IR Spectrometer (Nexus 470, Nicolet) in ATR mode. The spectra are visualized and evaluated by the software Omnic V. 6.1A.

Raman spectra were recorded with an dispersive Raman spectrometer (RXN1 workstation equipped with a $P^hAT$ solid state probe, 6 mm spot size, Kaiser Optical Systems Ltd.) equipped with a 400 mW diode-Laser (wavelength: 785 nm) and a peltier-cooled CCD-Detector. The spectra are evaluated and plotted by the software OPUS V. 4.2 from Bruker Optics.

The thermogravimetric analyses were performed with a TGA Q500 V6.4 Build 193 (Instruments Thermal Analysis). Open platinum pans were used and the measurements were performed in a nitrogen gas flow of 50 mL/min. The samples were measured isothermally at 25° C. for 60 min and the heated to 250° C. using a heating rate of 10K/min. The measured data was evaluated via the software Universal V4.2E.

The water sorption experiments were performed with a SPS11-10µ (Projekt Messtechnik). Open aluminium pans were used and the measurements were performed at 25° C. The measured data was evaluated via the software Excel (Microsoft).

Long Term Stability

The following tables 2 and 3 show data for the storage stability of crystalline compound of formula I in comparison to amorphous material of formula II. Samples of the compounds of formula I and II were packed into glass vials. Chemical stability was monitored over a period up 28 days under different conditions as indicated at each table.

TABLE 2

Storage condition:
Container: closed glass vials
Temperature: +40° C.

| | Crystalline hydrate I | | Amorphous sample | |
|---|---|---|---|---|
| Time Initial | Puirity (area %) | Total increase (area %) | Puirity (area %) | Total increase (area %) |
| Initial | 97.5 | — | 97.0 | — |
| 7 d | 97.2 | 0.3 | 96.5 | 0.5 |
| 14 d | 97.1 | 0.4 | 96.1 | 0.9 |
| 28 d | 97.0 | 0.5 | 95.6 | 1.4 |

TABLE 3

Storage condition:
Container: open glass vials
Temperature: +40° C., 75% relative humidity

| | Crystalline hydrate I | | Amorphous sample | |
|---|---|---|---|---|
| Time Initial | Puirity (area %) | Total increase (area %) | Puirity (area %) | Total increase (area %) |
| Initial | 97.3 | — | 97.0 | — |
| 7 d | 97.3 | ≤0.2 | 96.2 | 0.5 |
| 14 d | 97.3 | ≤0.2 | 95.9 | 1.1 |
| 28 d | 97.3 | ≤0.2 | 95.5 | 1.5 |

The crystalline hydrate of formula I shows reversible humidity dependent phase transitions which were investigated in a humidity chamber. To the crystalline hydrate of formula I as described herein Phase B is assignated.

XRPD—Humidity Chamber

The samples were subjected to a pre-defined humidity program lasting 48 hours in an SMS VGI-2000 chamber at a constant temperature of 25° C. XRPD patterns were collected continuously with a data collection time of between 6 and 11 min. (The amorphous sample was treated with the humidity-program reversed: first rising the humidity to 95%, then lowering it to 0% and rising to 95% again.).

| Humidity run | |
|---|---|
| Time [h] | r.h. [%] |
| 0 | 50 |
| 6 | 0 |
| 12 | 0 |
| 24 | 95 |
| 30 | 95 |
| 42 | 0 |
| 48 | 0 |

The results of humidity-resolved XRPD are shown in FIG. 11: phase transitions are visible after about 6, 13, 14 and 42 hours. The XRPD pattern of the starting phase B transformed to another phase C when the humidity was lowered to about 2%; this phase remained stable until the humidity was again raised to about 10% where an intermediate phase D formed which transformed back into the starting phase at around 20% rel. hum.

Solvate Formation

A given amount (~20-30 mg) of crystalline hydrate of formula I (Form B) was introduced in acetonitrile and slurry for 1 week. The wet solid material was analyzed as well by XRPD. In the experiment a single crystal sample was identified, which crystal structure was determined. The calculated structure is given in FIG. 12.

TABLE 4

| Crystal data | |
|---|---|
| Empirical formula | $C_{27}H_{40}FN_3O_9 \cdot C_2H_3N$ |
| Formula weight | 610.67 |
| Temperature | 293 K |
| Crystal system | Orthorhombic |
| Space group | $P\ 2_1 2_1 2_1$ |
| Unit cell dimensions | a [Å] 8.417(1) |
| | b [Å] 14.786(3) |
| | c [Å] 25.660(4) |
| | V [Å3] 3193.5(9) |
| | Z 4 |
| | Dc [g/cm3] 1.270 |

The invention claimed is:

1. A crystalline hydrate of the formula I,

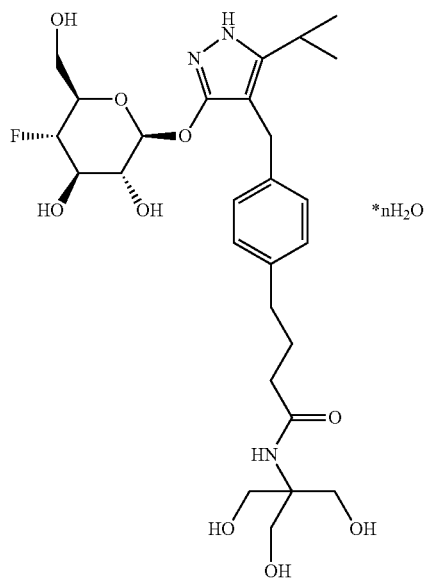

in which n has a value of from 2.1 to 2.5.

2. The crystalline hydrate of the formula I as claimed in claim 1 wherein n has a value of 2.25.

3. The crystalline hydrate of the formula I as claimed in claim 1 wherein the XRPD, measured with CuKα radiation, has a main peak of 5.8 degrees 2 theta±0.2 degrees 2 theta.

4. The crystalline hydrate of the formula I as claimed in claim 1 wherein the XRPD, measured with CuKα radiation, has at least peaks of the following 2 theta values:
5.8, 10.3, 14.2±0.2 degrees 2 theta.

5. The crystalline hydrate of the formula I as claimed in claim 1 wherein the XRPD, measured with CuKα radiation, has at least peaks of the following 2 theta values:
5.8, 7.1, 10.3, 14.2, 19.7±0.2 degrees 2 theta.

6. The crystalline hydrate of the formula I as claimed in claim 1 wherein the XRPD, measured with CuKα radiation, has at least peaks of the following 2 theta values:
5.8, 7.1, 10.3, 14.2, 19.9, 19.7, 21.8±0.2 degrees 2 theta.

7. A pharmaceutical composition comprising the crystalline hydrate of claim 1.

8. The pharmaceutical composition of claim 7, wherein said composition is in solid form.

9. The pharmaceutical composition of claim 7, further comprising one or more blood glucose-lowering active ingredients.

10. The pharmaceutical composition of claim 8, further comprising one or more blood glucose-lowering active ingredients.

11. A method of treating type 1 and type 2 diabetes in a patient in need thereof comprising administering to said patient a therapeutically effective amount of the pharmaceutical composition of claim 7.

12. A method of lowering blood glucose in a patient in need thereof comprising administering to said patient a therapeutically effective amount of the pharmaceutical composition of claim 7.

13. A method of treating type 1 and type 2 diabetes in a patient in need thereof comprising administering to said patient a therapeutically effective amount of the pharmaceutical composition of claim 9.

14. A method of lowering blood glucose in a patient in need thereof comprising administering to said patient a therapeutically effective amount of the pharmaceutical composition of claim 9.

15. A process for preparing the pharmaceutical composition of claim 7, comprising mixing the active ingredient with a pharmaceutically suitable carrier and converting this mixture into a form suitable for administration.

\* \* \* \* \*